(12) United States Patent
Yangdai et al.

(10) Patent No.: US 11,116,389 B2
(45) Date of Patent: Sep. 14, 2021

(54) GASTROINTESTINAL SAMPLING CAPSULE

(71) Applicant: ANKON TECHNOLOGIES CO., LTD, Wuhan (CN)

(72) Inventors: Tianyi Yangdai, Wuhan (CN); Yuhui Bao, Shanghai (CN)

(73) Assignee: ANKON MEDICAL TECHNOLOGIES (SHANGHAI) CO., LTD., Shanghai (CN)

(*) Notice: Subject to any disclaimer, the term of this patent is extended or adjusted under 35 U.S.C. 154(b) by 194 days.

(21) Appl. No.: 16/678,312

(22) Filed: Nov. 8, 2019

(65) Prior Publication Data
US 2020/0146541 A1    May 14, 2020

(30) Foreign Application Priority Data
Nov. 9, 2018    (CN) .......................... 201811330328.4

(51) Int. Cl.
A61B 5/15    (2006.01)
A61B 1/04    (2006.01)
A61B 1/00    (2006.01)
A61B 10/00   (2006.01)

(52) U.S. Cl.
CPC .......... *A61B 1/041* (2013.01); *A61B 1/00016* (2013.01); *A61B 10/0045* (2013.01); *A61B 2010/0061* (2013.01)

(58) Field of Classification Search
CPC ................ A61B 1/041; A61B 1/00016; A61B 2010/0061; A61B 1/00064; A61B 1/0661; A61B 1/00009; H04N 7/18; G06F 19/321
See application file for complete search history.

(56) References Cited

U.S. PATENT DOCUMENTS

| | | | |
|---|---|---|---|
| 10,172,598 B2 * | 1/2019 | Amoako-Tuffour | A61B 10/04 |
| 2017/0252018 A1 * | 9/2017 | Wrigglesworth | A61B 5/6861 |
| 2018/0164221 A1 * | 6/2018 | Singh | A61K 49/0058 |
| 2019/0274663 A1 * | 9/2019 | Rees | A61B 10/0045 |

* cited by examiner

*Primary Examiner* — Thai Q Tran
*Assistant Examiner* — Jose M Mesa
(74) *Attorney, Agent, or Firm* — Treasure IP Group, LLC

(57) ABSTRACT

The present invention provides a gastrointestinal sampling capsule includes an enclosure, a sampling port on the enclosure and a sampling module connected to the enclosure. The sampling port includes a plurality of sampling holes, and the sampling module includes a sample chamber and a sampling trigger unit which controls a connection or disconnection between the sampling port and the sample chamber to turn on sampling or turn off sampling. The gastrointestinal sampling capsule further includes a connecting passage arranged between the sample chamber and the sampling port, wherein an inlet of the connecting passage corresponds to the sampling port and an outlet of the connecting passage is connected to the sample chamber. A gap is provided between the plurality of sampling holes and the inlet of the connecting passage, through which the plurality of sampling holes are connected to the connecting passage.

11 Claims, 2 Drawing Sheets

GASTROINTESTINAL SAMPLING CAPSULE

CROSS REFERENCE TO RELATED APPLICATION

This application claims priority to a Chinese Application No. 201710316124.4, filed on May 8, 2017. Both the PCT application and Chinese Application are incorporated herein by reference in their entireties.

FIELD OF INVENTION

The present invention relates to a medical device, and more particularly to a gastrointestinal sampling capsule.

BACKGROUND

Due to high reliability and high safety, gastrointestinal sampling capsule has become an effective device for the diagnosis of gastrointestinal diseases and has obtained high recognition in the international medical device field. A gastrointestinal sampling capsule comprises an imaging unit, a data processing unit, a wireless transmission unit, and the like. Swallowed by a subject, the capsule can take images of stomach or intestine while traveling through GI tract of the subject, and transmit the images via the wireless transmission unit to an external receiving unit. The images can be displayed on a display device. Based on the displayed images, a physician can make a diagnosis of gastrointestinal diseases for the subject in a state of painless and non-invasive gastrointestinal peristalsis.

In addition, the gastrointestinal sampling capsule can also collect liquid inside stomach or intestine for subsequent detection, thereby providing basis for diagnosis of gastrointestinal diseases of the subject. In the existing gastrointestinal sampling capsules, a passive sampling method may be used, which generally rely on the self-flow of liquid in GI tract, extrusion by intestinal peristalsis or the use of materials with liquid adsorption capability to collect liquid, and is difficult to ensure collection of enough sample and difficult to predict collection time. Active sampling method may also be used, in which the time for triggering the capsule is controllable and sampling power is provided. Compared with the passive sampling method, active sampling method has many advantages: larger sampling power, faster sampling and higher controllability. However, some problems also exist: sampling hole or sampling tube is blocked, and sampling hole is exposed to the air during sampling, which can cause a failure of sampling. That is to say, the existing gastrointestinal sampling capsules have the problems of "Being blocked" and "Sucking air", with high sampling failure rate and limited operating environment. Although it is possible to empty intestine before sampling to reduce residues, the composition of intestinal liquid may be destroyed and the subsequent analysis may be affected.

It is necessary to provide an improved gastrointestinal sampling capsule to solve the said problem.

SUMMARY OF THE INVENTION

The present invention provides a gastrointestinal sampling capsule which can improve sampling effectiveness.

In one embodiment, the present invention provides a gastrointestinal sampling capsule comprising an enclosure, a sampling port on the enclosure and a sampling module connected to the enclosure, wherein the sampling port comprises a plurality of sampling holes, and the sampling module comprises a sample chamber and a sampling trigger unit which controls a connection or disconnection between the sampling port and the sample chamber to turn on sampling or turn off sampling. The gastrointestinal sampling capsule further comprises a connecting passage arranged between the sample chamber and the sampling port, wherein an inlet of the connecting passage corresponds to the sampling port and an outlet of the connecting passage being connected to the sample chamber; and a gap provided between the plurality of sampling holes and the inlet of the connecting passage, through which the plurality of sampling holes are connected to the connecting passage.

In one embodiment, the plurality of sampling holes are all cut in a wall of the enclosure and distributed along circumference of the enclosure within a predetermined range.

In one embodiment, the diameter of the sampling holes is smaller than the inner diameter of the connecting passage, and the number of the sampling holes is a selected value from 3 to 7.

In one embodiment, the sampling port is connected to a filter, and the plurality of sampling holes are constructed as an access of the filter.

In one embodiment, the present invention further comprises a control unit and a detection unit connected to the control unit arranged inside the enclosure, wherein the control unit is connected to the sampling trigger unit, the detection unit detects an external environment of the enclosure, and the control unit controls the sampling trigger unit to turn on sampling or turn off sampling according to the detection result or an external command.

In one embodiment, the detection unit comprises a camera, and a window corresponding to the camera is set on the enclosure adjacent to the sampling port and aligned with the sampling port in orientation.

In one embodiment, the enclosure comprises a first casing, a second casing and a third casing which are sequentially connected, wherein the first casing houses the sample chamber and the sampling trigger unit, the sampling port is configured on the second casing and the connecting passage is fixed in the second casing, and the detection unit is set in the third casing.

In one embodiment, the present invention further comprises a magnetic component configured in the enclosure, wherein the magnetic component is fixed to an inner wall of the enclosure and located between the sampling port and the sample chamber.

In one embodiment, the magnetic component is fixed in a space between the connecting passage and the sample chamber relative to the enclosure.

In one embodiment, the connecting passage is configured as a connecting tube, and the connecting tube is arranged in an L shape connecting the sample chamber to the sampling port.

In one embodiment, the connecting tube is attached to the inner wall of the enclosure along a radial direction of the gastrointestinal sampling capsule, and the connecting tube has a cross-sectional area smaller than an inner sectional area of the enclosure.

The gastrointestinal sampling capsule disclosed herein comprises a sampling port which comprises a plurality of sampling holes. Between the plurality of sampling holes and the inlet of the connecting passage is a gap arranged to form a filter structure between the sampling port and the connecting passage, thereby considerably reducing the probability that the residues occlude the sampling holes or tubes during active sampling, that is, reducing the sampling failure rate. Liquid environment around the sampling port is determined by the images captured by a camera to avoid sucking air and reduce sampling failure rate. Through internal and external magnetic fields, the orientation of the sampling holes can be actively adjusted and the posture and position of the gastrointestinal sampling capsule during sampling can be fixed to ensure liquid collection and improve sampling success rate.

DETAILED DESCRIPTION

The present invention can be described in detail below with reference to the accompanying drawings and preferred embodiments. However, the embodiments are not intended to limit the invention, and the structural, method, or functional changes made by those skilled in the art in accordance with the embodiments are included in the scope of the present invention.

Figure 1:
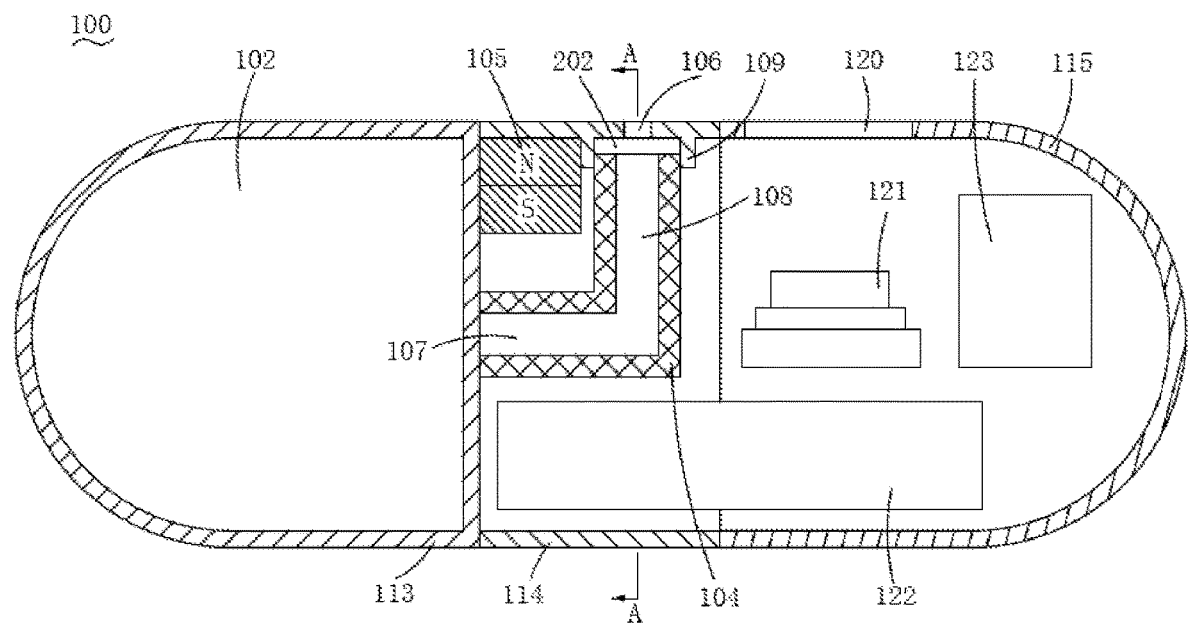
FIG. 1 is a cross-sectional view showing one preferred embodiment of a gastrointestinal sampling capsule according to the present invention.
Figure 2:
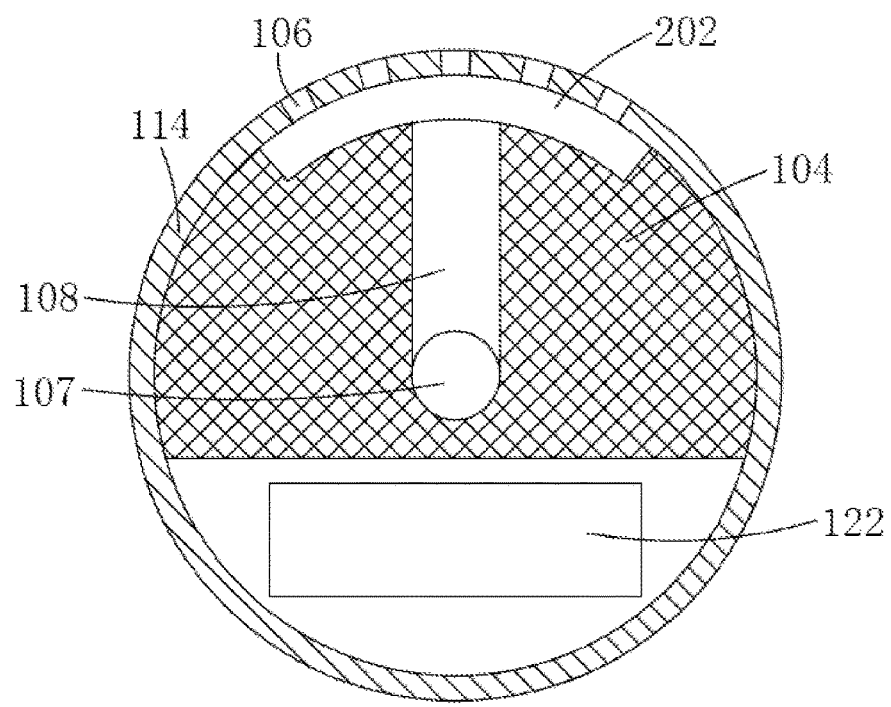
FIG. 2 is a cross-sectional view of the gastrointestinal sampling capsule taken along the line A-A shown in FIG. 1.

Referring to FIG. 1 and FIG. 2, showing a preferred embodiment of the present invention. A gastrointestinal sampling capsule 100 has an overall length which is not greater than 30 mm and a diameter which is not greater than 12 mm Preferably, the length is not greater than 27 mm. The gastrointestinal sampling capsule 100 comprises an enclosure, a sampling port on the enclosure and a sampling module connected to the enclosure. The sampling port comprises a plurality of sampling holes 106, and the sampling module comprises a sample chamber 102 and a sampling trigger unit which controls a connection or disconnection between the sampling port and the sample chamber 102 to turn on sampling or turn off sampling. A connecting passage 104 is arranged between the sample chamber 102 and the sampling port, the inlet of the connecting passage 104 corresponds to the sampling port and the outlet of the connecting passage 104 is connected to the sample chamber 102. A gap 202 is provided between the plurality of sampling holes 106 and the inlet of the connecting passage 104, through which the plurality of sampling holes 106 are connected to the connecting passage 104. The gap 202 allows liquid flowing in through different sampling holes 106 to flow into the connecting passage 104 and thereby into the sample chamber 102.

The sample chamber 102 can be formed by at least a portion of the enclosure, or can be a separate chamber configured inside the enclosure. Preferably, the sample chamber 102 is a vacuum container, that is, the sample chamber 102 has a vacuum environment inside before sampling, or the sample chamber 102 is constructed as a vacuum chamber with a volume that is not smaller than 0.3 mL for collecting sufficient sample liquid. The vacuum sample chamber provides active sampling power. In addition, the sampling module can further comprise a sampling power unit. The sampling power unit can be, but not limited to, a micro motor or a spring to drive a piston structure for liquid drawing as long as sampling can be made. The sampling trigger unit can be a control gate that controls sampling to start and end.

In the embodiment, the plurality of sampling holes 106 are all cut in a wall of the enclosure and distributed along the circumference of the enclosure within a predetermined range. Thus, the enclosure and the plurality of sampling holes 106 function as a filter ring. Configuration of a filtering structure greatly reduces the probability that residues occlude the sampling holes or tubes during active sampling, that is, sampling failure rate is lowered. The filtering structure can be any anti-blocking structure or a filter ring design, not limited to the structure defined in the embodiment. For example, the sampling port can be configured as a relatively large opening, the sampling port can be connected to a filter, and the plurality of sampling holes can be constructed as an access of the filter, which also makes it is possible to prevent blockage of the connecting passage.

The gastrointestinal sampling capsule 100 further comprises a control unit and a detection unit connected to the control unit arranged inside the enclosure. The control unit is connected to the sampling trigger unit, the detection unit detects an external environment of the enclosure and the control unit controls the sampling trigger unit to turn on sampling or turn off sampling according to detection result or an external command. Liquid environment around the sampling port is determined by a real-time monitoring performed in an external environment of the enclosure to avoid sucking air and reduce sampling failure rate.

Preferably, the control unit comprises a processor 123, the detection unit comprises a camera 121 and the enclosure is designed with a window 120 corresponding to the camera 121. The window 120 is close to the sampling port and is aligned with the sampling port in orientation. In this way, the field of view of lens of the camera 121 is aligned with and close to the sampling port, so that the images taken by the camera can be viewed to check liquid environment around the sampling port and determine whether the sampling port is immersed in liquid.

Referring to FIG. 1, the connecting passage 104 is configured as a connecting tube, and the connecting tube is arranged in an L shape connecting the sample chamber 102 to the sampling port. That is, the connecting passage 104 comprises a first section of through hole 107 along the axis of the gastrointestinal sampling capsule and a second section of through hole 108 along the diameter of the gastrointestinal sampling capsule, which constitute an L-shaped connecting tube. In addition, the gastrointestinal sampling capsule further comprises a magnetic component 105 configured inside the enclosure, and the magnetic component 105 is fixed to a position in the vicinity of the sampling port. The magnetic component 105 is configured to adjust the posture of the gastrointestinal sampling capsule and the orientation of the sampling port. In the embodiment, the magnetic component 105 is fixed to inner wall of the enclosure and is located between the sampling port and the sample chamber 102. The method facilitates an interaction between an external magnetic field (as generated by a permanent magnet) and the magnetic component 105 to adjust the posture of the gastrointestinal sampling capsule and the orientation of the sampling port, so as to submerge the sampling port in liquid and hold the gastrointestinal sampling capsule in place.

Specifically, the enclosure comprises a first casing 113, a second casing 114 and a third casing 115 which are sequentially connected. The first casing 113 houses the sample chamber 102 and the sampling trigger unit. The sampling port is configured on the second casing 114 and the connecting passage is fixed in the second casing 114. The camera 121 is arranged in the third casing 115 and the window 120 corresponding to the camera 121 is also cut in the third casing 115. The three casings are assembled to simplify the manufacturing process of the gastrointestinal sampling capsule. In the embodiment, two fixing ribs 109 are mounted on the inner wall of the second casing 114 with a space, and the connecting passage 104 is interference-fitted with the two fixing ribs 109 to be fixed between the two fixing ribs 109. The magnetic component 105 is limited using the first casing 113 and one of the fixing ribs 109 so that the magnetic component 105 is just accommodated in the space between the connecting passage 104 and the first casing 113.

In addition, other circuit components are arranged in the second casing 114 and the third casing 115 of the gastrointestinal sampling capsule, such as a battery 122 and a wireless communication module. The processor 123 is arranged in the third casing 115, and the camera 121 and the wireless communication module are all connected to the processor 123. At least part of the circuit components are arranged in the second casing 114, such as the battery 122, to make reasonable use of the space inside the enclosure, so that the overall structure of the gastrointestinal sampling capsule is more compact.

Referring to FIG. 2, the connecting passage 104 is closely attached to the inner wall of the second casing 114 for fixing and waterproofing purposes. A plurality of sampling holes 106 are cut in the second casing 114 in a predetermined sectorial range. In the embodiment, the number of sampling holes is 5, and the preferred number of the sampling holes can be 3~7. The diameter of the sampling holes 106 is smaller than the diameter of the first section of through hole 107 and the second section of through hole 108. For example, the diameter of each sampling hole 106 is smaller than or equal to 0.5 mm, and the diameter of the first section of through hole 107 and the second section of through hole 108 is 0.7 mm~1.0 mm. The gap 202 allows liquid flowing in through different sampling holes 106 to flow into the T-shaped tube and thereby into the sample chamber 102. Thus, the second casing 114 and the plurality of sampling holes 106 function as a filter ring. The cross-sectional area of the connecting passage 104 is smaller than the inner cross-sectional area of the second casing 114, so that the remaining space can be filled with other components, such as the battery 122 shown in FIG. 1.

Figure 3:
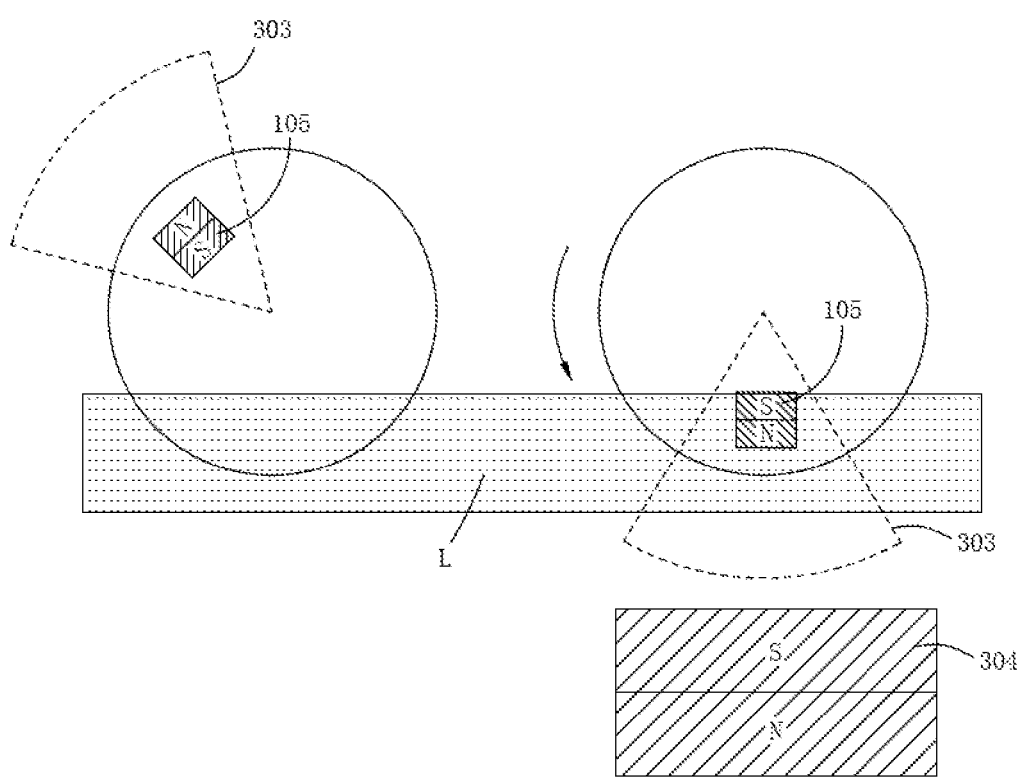
FIG. 3 is a schematic view showing an external control for posture adjustment of the gastrointestinal sampling capsule as shown in FIG. 1.

The principle of the gastrointestinal sampling capsule in the embodiment to prevent suction of air can be described in detail below with reference to FIG. 3. If there is less liquid in a cavity or due to wrinkles in a cavity, the sampling port of the gastrointestinal sampling capsule may be exposed to air, as shown in the left side of FIG. 3. If sampling is turned on at this point, a large amount of air can be sucked into the gastrointestinal sampling capsule, resulting in insufficient collection of liquid or sampling failure. Mark number 303 in FIG. 3 denotes a distribution direction of the plurality of sampling holes 106 and a field of view of the camera 121. At this point, the images taken by the camera 121 can be viewed to check the surrounding environment, so as to prohibit sampling from being triggered. Then, an interaction between an external magnetic field (as generated by a permanent magnet 304) and the magnetic component 105 in the gastrointestinal sampling capsule can be utilized to adjust the posture of the gastrointestinal sampling capsule and the orientation of the sampling port, so as to submerge the sampling port in liquid and hold the gastrointestinal sampling capsule in place, as shown in the right side of FIG. 3. Sampling cannot be turned on until it is determined through the images taken by the camera 121 that sampling port is submerged in liquid.

When the gastrointestinal sampling capsule 100 is used, the camera 121 captures images of surrounding environment in real time, transmits the images to the processor or transmits the images via the wireless transmission module to an external device for display. These images can be used for three purposes: first, monitoring GI tract environment for diagnosis; second, identifying regions of GI tract for positioning; and third, determining the liquid environment around the sampling port. When it is found that the gastrointestinal sampling capsule is reached a target area, such as the small intestine, while the surrounding is full of liquid, sampling can be triggered by a program or started by a command sent from the external device. If it is found that liquid around is insufficient, the external device such as the permanent magnet 304 can be used to actively adjust the posture of the gastrointestinal sampling capsule and the orientation of the sampling port until it is determined that there is sufficient liquid around. Finally, the gastrointestinal sampling capsule is held in place by attraction of the external permanent magnet 304 to start sampling. The above operations, including data acquisition, data processing, determination, command transmission and external device control, can also be completely handled by a computer to achieve automation.

In the embodiment, configuration of a filtering structure greatly reduces the probability that the residues occlude the sampling holes or tubes during active sampling, that is, the sampling failure rate is lowered. Liquid environment around the sampling port is determined by images captured by the camera to avoid sucking air and reduce sampling failure rate, and through internal and external magnetic fields, the orientation of the sampling port can be actively adjusted and the posture and position of the gastrointestinal sampling capsule during sampling can be fixed to ensure liquid collection and improve sampling success rate.

It should be noted that the enclosure is not limited to the shape as shown in the figure, but may be in the shape of a rugby or other shapes. Alternatively, the magnetic component can be drive component that can cooperate with an external control device to drive the gastrointestinal sampling capsule to move.

It should be understood that, although the specification is described in terms of embodiments, not every embodiment merely includes an independent technical solution. Those skilled in the art should have the specification as a whole, and the technical solutions in each embodiment may also be combined as appropriate to form other embodiments that can be understood by those skilled in the art.

The present invention by no means is limited to the preferred embodiments described above. On the contrary, many modifications and variations are possible within the scope of the appended claims.

What is claimed is:

1. A gastrointestinal sampling capsule, comprising:
   an enclosure, a sampling port on the enclosure and a sampling module connected to the enclosure, wherein the sampling port comprises a plurality of sampling holes, and the sampling module comprises a sample chamber and a sampling trigger unit which controls a connection or disconnection between the sampling port and the sample chamber to turn on sampling or turn off sampling;
   and further comprising a connecting passage arranged between the sample chamber and the sampling port, wherein an inlet of the connecting passage corresponds to the sampling port and an outlet of the connecting passage being connected to the sample chamber; and a gap provided between the plurality of sampling holes and the inlet of the connecting passage, through which the plurality of sampling holes are connected to the connecting passage.

2. The gastrointestinal sampling capsule of claim 1, wherein the plurality of sampling holes are all cut in a wall of the enclosure and distributed along circumference of the enclosure within a predetermined range.

3. The gastrointestinal sampling capsule of claim 2, wherein the diameter of the sampling holes is smaller than the inner diameter of the connecting passage, and the number of the sampling holes is a selected value from 3 to 7.

4. The gastrointestinal sampling capsule of claim 1, wherein the sampling port is connected to a filter, and the plurality of sampling holes are constructed as an access of the filter.

5. The gastrointestinal sampling capsule of claim 1, further comprising a control unit and a detection unit connected to the control unit arranged inside the enclosure, wherein
the control unit is connected to the sampling trigger unit,
the detection unit detects an external environment of the enclosure, and
the control unit controls the sampling trigger unit to turn on sampling or turn off sampling according to the detection result or an external command.

6. The gastrointestinal sampling capsule of claim 5, wherein the detection unit comprises a camera, and a window corresponding to the camera is set on the enclosure adjacent to the sampling port and aligned with the sampling port in orientation.

7. The gastrointestinal sampling capsule of claim 5, wherein the enclosure comprises a first casing, a second casing and a third casing which are sequentially connected, wherein
the first casing houses the sample chamber and the sampling trigger unit,
the sampling port is configured on the second casing and the connecting passage is fixed in the second casing, and
the detection unit is set in the third casing.

8. The gastrointestinal sampling capsule of claim 1, further comprising a magnetic component configured in the enclosure, wherein the magnetic component is fixed to an inner wall of the enclosure and located between the sampling port and the sample chamber.

9. The gastrointestinal sampling capsule of claim 8, wherein the magnetic component is fixed in a space between the connecting passage and the sample chamber relative to the enclosure.

10. The gastrointestinal sampling capsule of claim 1, wherein the connecting passage is configured as a connecting tube, and the connecting tube is arranged in an L shape connecting the sample chamber to the sampling port.

11. The gastrointestinal sampling capsule of claim 10, wherein the connecting tube is attached to the inner wall of the enclosure along a radial direction of the gastrointestinal sampling capsule, and the connecting tube has a cross-sectional area smaller than an inner sectional area of the enclosure.

* * * * *

UNITED STATES PATENT AND TRADEMARK OFFICE
CERTIFICATE OF CORRECTION

PATENT NO. : 11,116,389 B2  
APPLICATION NO. : 16/678312  
DATED : September 14, 2021  
INVENTOR(S) : Yangdai et al.

Page 1 of 1

It is certified that error appears in the above-identified patent and that said Letters Patent is hereby corrected as shown below:

On the Title Page

Item (73) should read:  
Ankon Technologies Co., LTD. Wuhan (CN)

Signed and Sealed this  
Sixth Day of September, 2022

Katherine Kelly Vidal  
*Director of the United States Patent and Trademark Office*